United States Patent [19]

Friedman et al.

[11] 4,026,301
[45] May 31, 1977

[54] APPARATUS AND METHOD FOR OPTIMUM ELECTRODE PLACEMENT IN THE TREATMENT OF DISEASE SYNDROMES SUCH AS SPINAL CURVATURE

[75] Inventors: Harry G. Friedman, Plymouth; Robert W. Wickham, Jr., Harris, both of Minn.

[73] Assignee: Medtronic, Inc., Minneapolis, Minn.

[22] Filed: Apr. 21, 1975

[21] Appl. No.: 569,842

[52] U.S. Cl. .......................... 128/418; 128/419 R; 128/421

[51] Int. Cl.² ............................................. A61N 1/04

[58] Field of Search ........... 128/2.06 E, 2.1 E, 404, 128/418, 419 C, 419 E, 419 P, 419 R, 421, 422, 423, 2 B, 347, 303 B

[56] References Cited

UNITED STATES PATENTS

| | | | |
|---|---|---|---|
| 3,087,486 | 4/1963 | Kilpatrick | 128/418 |
| 3,598,108 | 8/1971 | Jamshidi et al. | 128/2 B |
| 3,737,579 | 6/1973 | Bolduc | 128/418 |
| 3,827,428 | 8/1974 | Hon et al. | 128/418 |

*Primary Examiner*—William E. Kamm
*Attorney, Agent, or Firm*—Lindquist & Vennum

[57] ABSTRACT

A system for the electrical treatment of spinal curvature through the exercise of selected spinal muscles. A probe having a blunt, muscle-penetrating tip is fitted with a sleeve such that its tip extends from the sleeve. A helical electrode is mounted on an elongated tool capable of imparting a rotational force to the electrode while allowing a disengagement with the electrode in the direction of its longitudinal axis. The probe is inserted in the paraspinal muscles and is removed while leaving the sleeve within the muscle. The electrode-tool assembly is inserted through the sleeve and the electrode secured in the paraspinal muscles by a rotational force applied to the tool. After electrode securement, the tool is withdrawn from the sleeve and the sleeve withdrawn from the muscle leaving the electrode secured within the muscle. Needle electrodes may be employed to stimulate the paraspinal muscles at several sites to establish those sites at which the induced muscle contraction provides maximum correction of the spinal curvature and the blunt probe tip may be provided with an electrode for muscle stimulation at varied penetration depths to establish the optimum depth for securement of the helical electrode.

The electrodes are connected by leads to a receiver circuit implantable beneath the patient's skin and operable to receive RF modulated stimulation impulses transmitted through the skin. The impulses are developed by a patient operated RF transmitter with a cyclic on and off stimulation and rest periods so that stimulation of the muscles may take place while the patient relaxes or sleeps.

19 Claims, 10 Drawing Figures

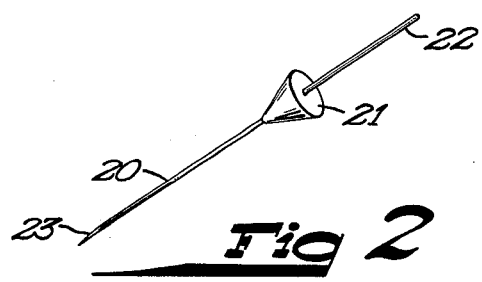
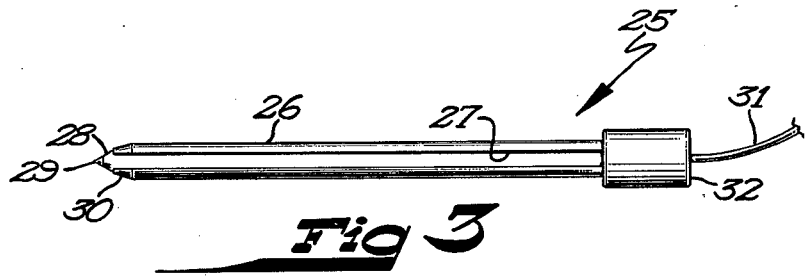
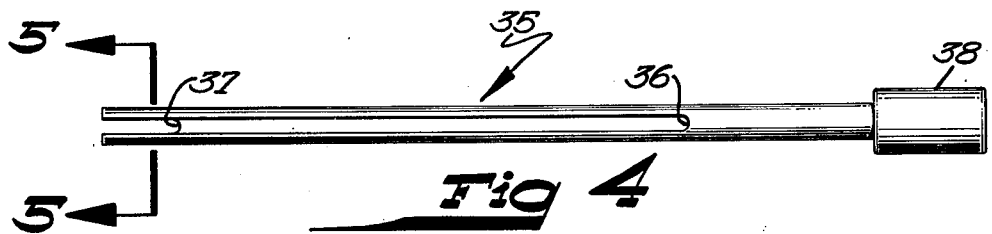
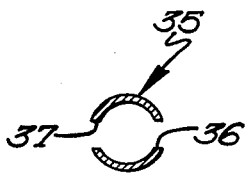
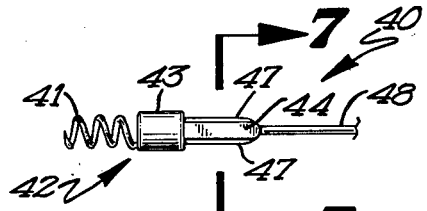
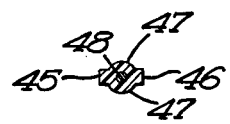
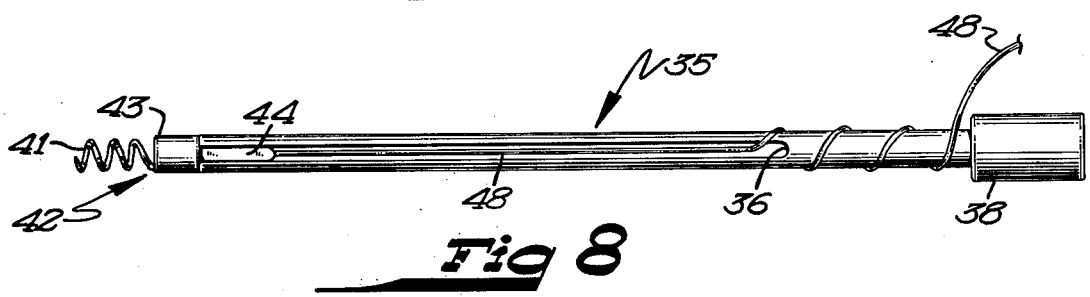

APPARATUS AND METHOD FOR OPTIMUM ELECTRODE PLACEMENT IN THE TREATMENT OF DISEASE SYNDROMES SUCH AS SPINAL CURVATURE

BACKGROUND OF THE INVENTION

Spinal curvature has been known to man since he first assumed the erect posture. Scoliosis, a lateral curvature of the vertebral column and rotation around its longitudinal axis, is a progressive condition often associated with other spinal curvatures; kyphosis or humpback and/or lordosis or swayback. Each of these conditions is debilitating and deforming to a degree depending on the characteristics and extent of the curvature.

Idiopathic scoliosis accounts for the vast majority of all scoliosis and is present in one out of ten children. While there is evidence that idiopatic scoliosis is genetic, its true cause has not been found. Also, there is no known preventative or cure for idiopathic scoliosis and treatment remains a matter of correcting the curvature after it has developed. The curvature in idiopathic scoliosis typically consists of a major curve, the curve of greatest degree, and a minor curve or curves which form as a compensating mechanism to keep the patient's head directly over the pelvis. In some instances, more than one major curve may develop.

Among the more successful treatments for idiopathic scoliosis are the long-term use of braces and spinal fusions. The bracing technique requires the almost constant wearing of a cumbersome external device over a period of several years. This type of treatment is very expensive and, at best, can only prevent a scoliotic curve from progressing. Thus, even the best bracing techniques fall far short of leaving the patient with a corrected mobile spine. In addition, because the brace is typically used during adolescence it has often left the patient with significant psychological problems.

In contrast to the bracing technique, various spinal fusion techniques have provided satisfactory correction of the spinal curvature in those patients, usually young, whose spines were flexible at the time of fusion. However, the patient is left with a rigid spine. Because these fusion techniques have been developed in relatively recent times, it is not known what effect a spinal fusion will have during the adult life of the patient. Also, the loss of mobility and disc spaces puts on ever increasing stress on those lower discs that remain mobile.

In addition to bracing and spinal fusion techniques, there are suggestions in the prior art of the use of electrical stimulation in the treatment of scoliosis. The suggestions are in terms of transcutaneous stimulation. Transcutaneous stimulation produces a contraction of at least the outer paraspinal muscles. These muscles are longer than the muscles deeper in the back and extend over many vertebral segments. Thus, while a transcutaneous stimulation of the paraspinal muscles may have a beneficial effect on the major spinal curve, the stimulation of the longer, outer paraspinal muscles has the tendency to worsen the compensating curve. The electrical treatment of spinal curvature is not an accepted practice and it is believed that the tendency to worsen the compensating curve attending a transcutaneous stimulation of the paraspinal muscles is a primary factor in the failure of such a treatment to gain recognition.

SUMMARY OF THE PRESENT INVENTION

The present invention provides a system for the electrical treatment of scoliosis, and other spinal curvatures, capable of producing a correction in the curvature without resort to cumbersome external bracing and without loss of spinal mobility and disc spaces. The present invention also overcomes the worsening of the compensating curve(s) attending known prior art electrical treatments.

The present invention consists essentially of sleeve means, means for positioning one end of the sleeve means within the paraspinal muscles and means insertable through the other end of the sleeve means for delivering and securing an electrode within the paraspinal muscles adjacent the one sleeve means end. The electrodes are connected to a source of stimulation impulses having alternating or cyclic stimulation and rest periods and stimulation of the muscles may take place while the patient relaxes or sleeps.

In an preferred embodiment, a probe having a blunt, muscle-penetrating tip is fitted with a sleeve such that its tip extends from the sleeve. The blunt tip allows a muscle penetration with a minimum of muscle damage through its ability to separate the muscles without severing them. The probe is inserted into the paraspinal muscle and removed while leaving the sleeve within the muscle.

A helical electrode is mounted on an elongated tool capable of imparting a rotational force to the electrode while allowing a disengagement with electrode in one direction along the longitudinal axis of the tool. The electrode-tool assembly is inserted through the sleeve and the electrode secured in the paraspinal muscles by a rotational force applied to the tool. After the electrode is secured, the tool is withdrawn from the sleeve and the sleeve withdrawn from the muscle leaving the electrode secured within the muscle.

Prior to positioning the probe, needle electrodes may be employed to evaluate the effect of paraspinal muscle contraction produced by stimulation of those muscles at several sites. When the needle electrode sites which maximize the correction of the spinal curvature have been determined, the blunt probes are inserted in those sites. The blunt probes may be provided with electrode tips and the paraspinal muscles again stimulated at varied penetration depths to establish the optimum depth for securement of the helical electrode. In this manner, the optimum site for the electrode as well as the optimum electrode depth is established and the electrode is secured at the established sites and to the established depths with a minimum of tissue damage.

BRIEF DESCRIPTION OF THE DRAWINGS

FIG. 2 illustrates a preferred embodiment of the needle electrode employed in the system of the present invention.

FIG. 3 illustrates a preferred embodiment of the probe-sleeve assembly employed in the system of the present invention.

FIG. 4 illustrates a preferred embodiment of the tool used to secure the electrode within the paraspinal muscles in the system of the present invention.

FIG. 5 illustrates a cross-section taken along the line 5—5 in FIG. 4.

FIG. 7 illustrates a cross-section taken along the line 7—7 in FIG. 6.

FIG. 8 illustrates the assembly of the preferred embodiments illustrated in FIGS. 4–7.

FIGS. 9 and 10 illustrate the schematic circuits of the electronic transmitter and receiver of the electro-spinal instrumentation system.

DETAILED DESCRIPTION OF THE DRAWINGS

Figure 1:
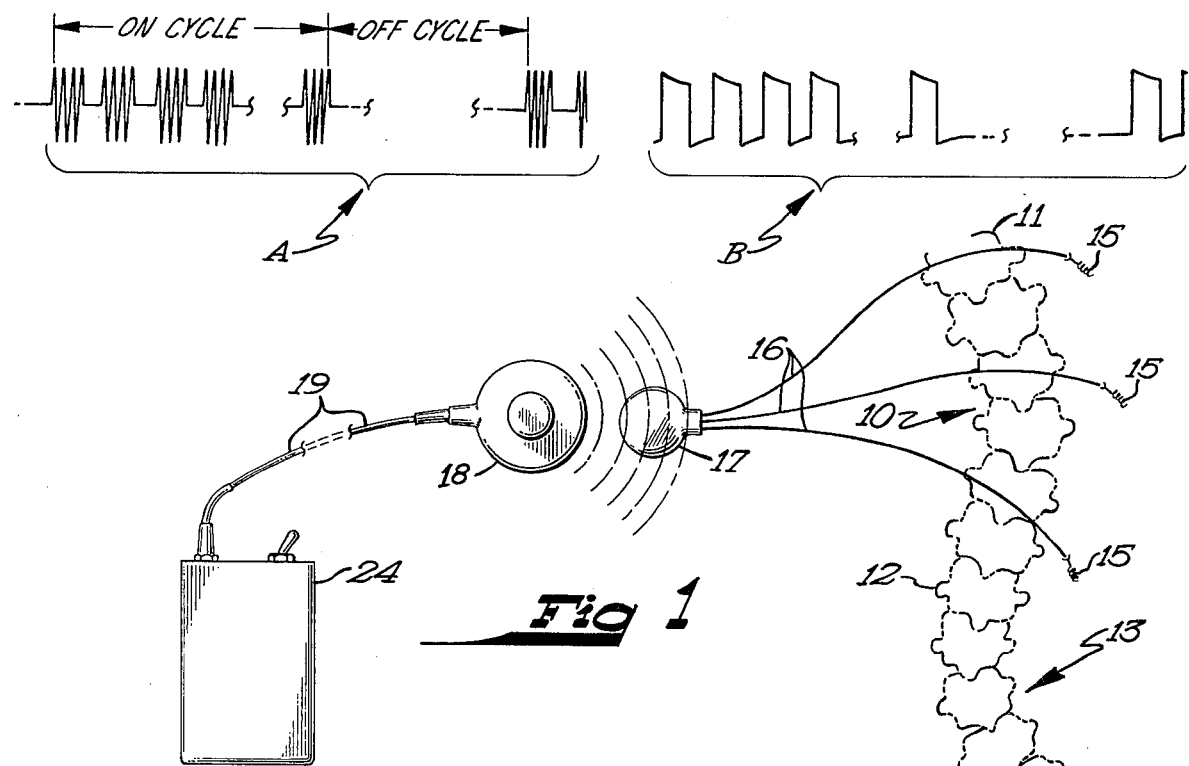
FIG. 1 is a diagrammatical illustration of a typical scoliotic curve of the spinal column and the electro-spinal instrumentation system of the present invention.

FIG. 1 is a diagrammatic illustration of the spinal column and a typical scoliotic curve under treatment by the electro-spinal instrumentation system of the present invention. The curve is composed of a thoracic curve 10 bounded by vertebra 11 and vertebra 12 and a lumbar curve 13 bounded by vertebra 12 and vertebra 14. Of course, the vertebrae 11, 12 and 14 which bound the curves 10 and 13 are dependent on the curves in question and may be any of the vertebrae in the spinal column. That is, vertebra 11 is the highest vertebra with its superior border inclined toward the thoracic concavity while vertebra 14 is the lowest vertebra with its inferior border inclined toward the lumbar concavity. Vertebra 12 is the lowest vertebra with its inferior border inclined toward the thoracic concavity and the highest vertebra with its superior border inclined toward the lumbar concavity. The vertebrae 11, 12 and 14, as determined by the above definitions, are commonly employed to measure the amount of curvature, the particular measurement methods being well known to those skilled in the art. In the spinal column illustrated, both the thoracic and lumbar curvatures are approximately 65° when measured by the Cobb method.

A typical scoliotic curve has a major curve and a minor curve or curves which form as a compensatory mechanism to maintain the head directly over the pelvis. The present invention is directed to a straightening of the major curve through an electrically induced contraction of the paraspinal muscles in proximity to the convexity of the major curve and without a contraction of those paraspinal muscles which extend sufficiently beyond the major curve to have a worsening effect on the compensatory curve. With reference to the curve 10 illustrated in FIG. 1, this is accomplished by placing the electrodes 15 within the deeper paraspinal muscles proximate the convex side of the curve (the right side for curve 10).

The electro-spinal instrumentation system illustrated in FIG. 1 is provided to exercise the paraspinal muscles to cause them to hypertrophy or strengthen through the application of electrical stimulating impulses to three electrodes 15, at least two of said electrodes being active electrodes and one of the electrodes being an indifferent electrode. The electrodes 15 are placed in a manner described hereinafter in greater detail at varying depths within the paraspinal muscles adjacent the major curve 10 of the spinal column. It is believed that these muscles through the application of electrical stimuli will hypertrophy and as a result induce a slight imbalance in comparison with the muscles on the concave side of the curve 10 through the remaining growing years of the child and that muscle imbalance will arrest, or work to correct the convexity of the spinal column 10.

The electrodes 15 are electrically connected to leads 16 that are electrically connected to a biocompatible, subcutaneously implanted, electronic radio frequency signal receiver 17.

The receiver 17 is placed subcutaneously in a surgical procedure to be described following the placement of the electrodes 15. The patient, in using the electrospinal instrumentation system, places a transmitting antenna 18 over the subcutaneous implant position of the receiver 17. The antenna 18 is electrically connected by a lead 19 to the output jack of a radio frequency pulse generating transmitter 24.

In operation by the patient, the radio frequency transmitter 24 is conveniently placed next to the patient's body while the patient is at rest, and the antenna 18 is taped in place over the antenna of the implanted reciver 17. Then the patient turns on the transmitter, and the transmitter 24 cyclically produces a train of stimulating impulses at a rate that is preset by the electronic circuitry of the transmitter.

The train of impulses produced by the transmitter 24 and transmitted by antenna 18 is depicted as wave form A in FIG. 1. Likewise, the impulses received by receiver 17 and applied to the electrodes 15 are depicted as wave form B in FIG. 1. During the "on" cycle of the transmitter 24, the train of pulses A is produced, each pulse having a preselected width and amplitude recurring at a preselected rate. During the "off" cycle, no pulses are produced, and the muscles are allowed to rest. The time periods of the on and off cycle may be one second and 5 seconds, respectively, which allows the stimulated muscles to contract, and relax without causing fatigue. The preselected rate, amplitude and pulse width of the stimulating pulses may comprise a rate of 30 pulses per second at an amplitude between the electrodes selectable from 0 to 10 volts and a pulse width of about 220 microseconds. These parameters are selectable by the surgeon at time of implant when the operation of the system is tested and may be altered by the surgeon post-operatively as the patient's progress is monitored.

Further details of the circuit of the pulse generator and receiver will be described in conjunction with FIGS. 9 and 10. The surgical procedure for implanting the receiver and electrodes will not be described.

After surgical incision and exposure of the paraspinal muscles, the first step in the performance of the system of the present invention is the identification of the optimal sites for the positioning of electrodes. The optimal electrode sites are defined as those sites which maximize the correction of the curvature as a result of an induced contraction of the paraspinal muscles. It is contemplated that the present invention will be carried out with three electrodes, two active electrodes and one indifferent electrode, although other numbers of electrodes may be successfully employed. Also, it is expected that the active electrodes will be negative inasmuch as this provides a lower stimulation threshold.

The optimization of the sites for electrode placement may be accomplished through the use of needle electrodes such as that illustrated in FIG. 2. The needle electrode may have a portion 20 formed similarly to a hypodermic needle and be provided with a knob 21 to facilitate its manipulation. The portion 20 is connected to an external source of stimulation energy through a lead 22 and may be provided with a cutting surface 23 to facilitate the placement of the electrode within the paraspinal muscles. It is contemplated that several alternative placements of the needle electrodes of FIG. 2 will be required to establish the optimal electrode sites, the sites which maximize straightening of the spinal curvature as a result of induced muscle contraction. The optimal sites may be established visibly by repeatedly repositioning the needle electrodes of FIG. 2 within the paraspinal muscles and electrically inducing a contraction of those muscles. Alternatively, the optimal sites can be established through X-ray techniques in which the degree of straightening is established, for several sites, by a measurement of the curvature during stimulation.

Once the optimal sites for electrode securement are established, the needle electrodes are withdrawn. A blunt probe fitted with a sleeve is then inserted within the muscle at each site established through the use of the needle electrodes. A preferred embodiment of a blunt probe which may be employed within the system of the present invention is illustrated at 25 in FIG. 3. The probe 25 has an elongated portion fitted with a sleeve 26 with the sleeve being provided with a slot 27 throughout its length. The probe terminates at a blunt tip 28 which extends from the sleeve 26 and is provided with an electrode 29 at its end. The electrode 29 is in electrical communication with a lead 31 through which it may be connected to a source of stimulation energy (not shown) and is spaced from the end of the sleeve 30 to contact the muscle at generally the same location as a permanent electrode inserted into the muscle through the sleeve 26. The probe may be provided with an enlarged portion 32 which acts as a stop for the sleeve 26 and as a handle to facilitate manipulation of the probe and the sleeve 26 may have a tapered portion 30 conforming the blunt tip 28 of the probe.

A blunt probe 25 is inserted within the paraspinal muscle at each site established as optimal through the use of the needle electrodes of FIG. 2. The blunt tip 28 of the probe allows a penetration of the paraspinal muscles through a separation of those muscles thereby minimizing the injury resulting from muscle penetration and the stop 32 causes the probe to carry the sleeve 26 into the muscle tissue. Each probe is inserted to various penetration depths and the muscle stimulated at each depth through a stimulating signal applied at the tip electrode 29. The penetration depth which maximizes the correction of the spinal curvature can be established visibly or through the use of X-ray techniques. Once the optimal penetration depth is established, the probe is withdrawn from the paraspinal muscle leaving the sleeve 26 in position in the muscle at the depth established for maximum curvature correction.

Referring now to FIG. 4, there is shown a tool 35 which is used to secure a helical electrode within the paraspinal muscles at the sites and penetration depths established with the needle electrode of FIG. 2 and the probe of FIG. 3. The tool 35 is essentially an elongated tubular member having two slots on opposing sides thereof. One slot 36 extends from one end of the tool 35 to a spot adjacent its other end to form a recess within the tool. The other slot 37 extends from the same end of the tool 35 as the slot 36 but need extend only far enough to accommodate the electrode to be discussed below. FIG. 5 is a cross-section taken along the line 5—5 in FIG. 4 and illustrates the slots 36 and 37 on opposing sides of the tool 35. The tool 35 may be provided with a handle 38 to facilitate its manipulation with the handle 38 being secured to the tool 35 in any convenient manner.

Figure 6:
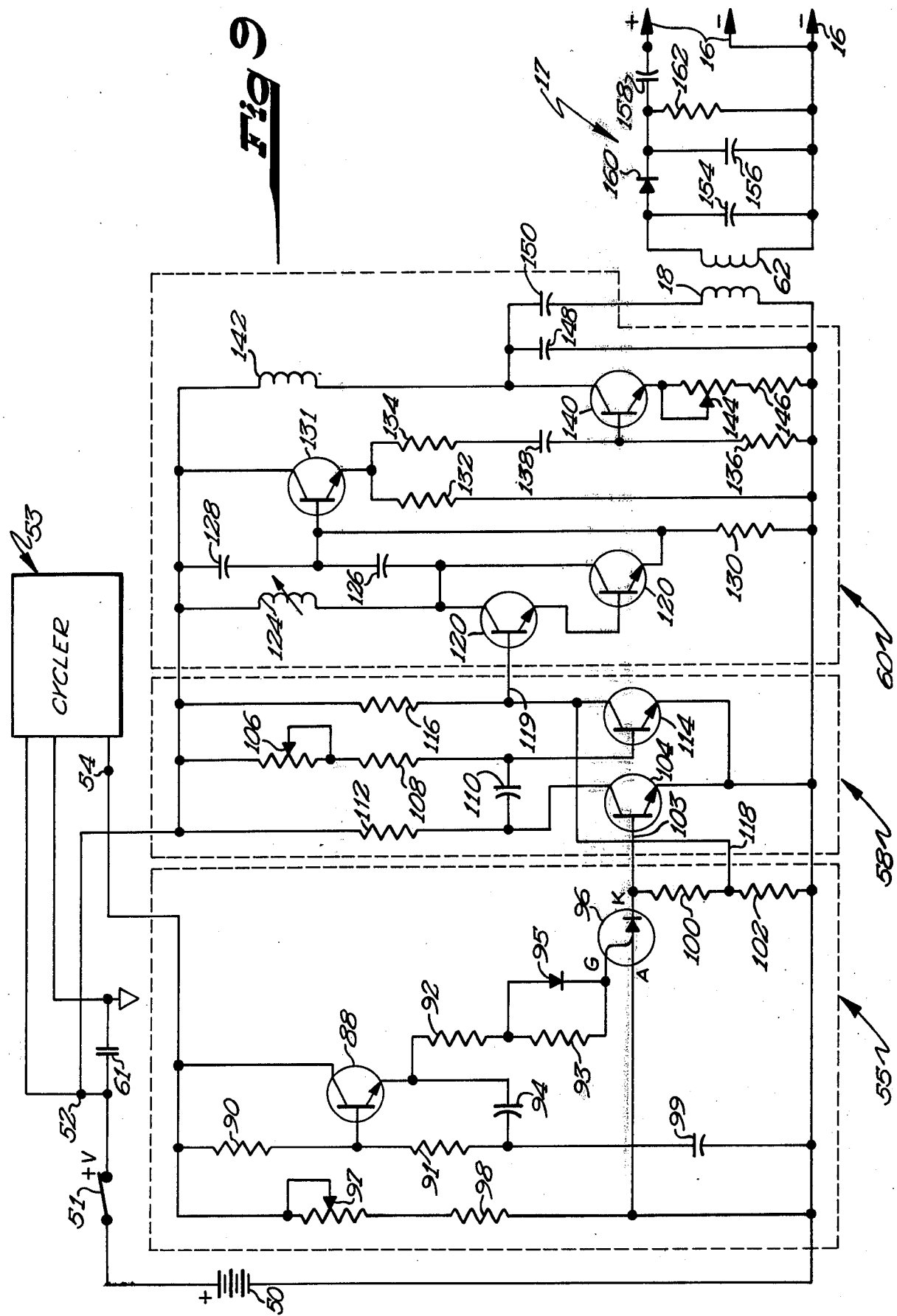
FIG. 6 illustrates a preferred embodiment of the electrode employed in the system of the present invention.

Referring now to FIG. 6, there is shown a helical electrode 40 which is a preferred electrode embodiment within the system of the present invention. The electrode 40 has an exposed, electrically-conductive helical or spiral member 41 which will engage and pentrate muscle tissue when rotated in the proper direction. The cooperation between the member 41 and the muscle tissue is analogous to the operation of a cork screw and electrodes such as that illustrated in FIG. 6 have been referred to in the prior art as cork screw electrodes. The member 41 extends from an electrode body 42 which has a first generally cyclindrical portion 43 and a generally flat or tab portion 44. The cylindrical portion 43 of the electrode body 42 has a diameter approximating that of the tool of FIG. 4 and the portion 44 of the electrode body 42 is composed of a central portion 47 which accommodates an electrically conductive lead 48 and extending members or wings, 45 and 46, which are sufficiently extensive to be accommodated within the slots 36 and 37 of the tool 35. The cork screw 41 is adapted for connection to an external source of stimulation energy via the lead 48, the lead 48 being encased in an electrical insulation in known manner.

Referring now to FIG. 8, there is shown the electrode 40 mounted on the tool 35. The wings 45 and 46 of the electrode body 42 are within the slots 36 and 37 of the tool 35 with the cylindrical portion 43 of the electrode body 42 in abutment with one end of the tool 35. With this tool and electrode configuration, tool 35 may be withdrawn from the electrode body 42 in one direction along its longitudinal axis while being capable of imparting a force to electrode body 42 in the other longitudinal direction and will transmit a rotational force to the electrode body 42 via the wings 45 and 46 in cooperation with the slots 36 and 37. The lead 48 lies within the slot 36 and emerges from the slot 36 at its end to be wrapped around the body of the tool 35. The direction of wrapping of the lead 48 around the body of the tool 35 is selected such that the lead 48 will unwrap itself from the tool 35 as the tool 35 is rotated in the direction which will cause a penetration of the muscle tissue by the cork screw 41. The number of wrappings may correspond with the number of coils in the member 41.

With the electrode 40 mounted on the tool 35 as illustrated in FIG. 8 and with the sleeve 26 in the optimal position relative to the paraspinal muscles, as described above, the tool-electrode combination is inserted within the sleeve 26, the tool 35 rotated thereby imparting a rotational force to the electrode 40 and causing a penetration of the muscle tissue by the cork screw 41 and tool 35 withdrawn from the sleeve leaving the electrode secured within the muscle. The electrode 29 of the probe 25 is spaced from the sleeve 26 during insertion such that the helical electrode will penetrate to the depth established as optimal during stimulation with the electrode 29.

With the tool 35 withdrawn, the sleeve 26 is also withdrawn from the muscle tissue with the slot 27 within the sleeve 26 allowing a disengagement of the sleeve 26 from the lead 48. Of course, if the end of lead 48 is free and the nature of its electrical connection to the external stimulation device (not shown) permits, the slot 27 in sleeve 26 may be eliminated inasmuch as the sleeve may be totally withdrawn over the lead 48. With the sleeve 26 withdrawn, the electrode 40 is in the optimal location to maximize the correction in the spinal curvature through an electrically induced contraction of the paraspinal muscles. While the electrodes are in direct contact with the muscle tissue, it is believed that contraction of the muscle is induced chiefly through nerve stimulation as a result of a lower nerve threshold.

Figure 10:
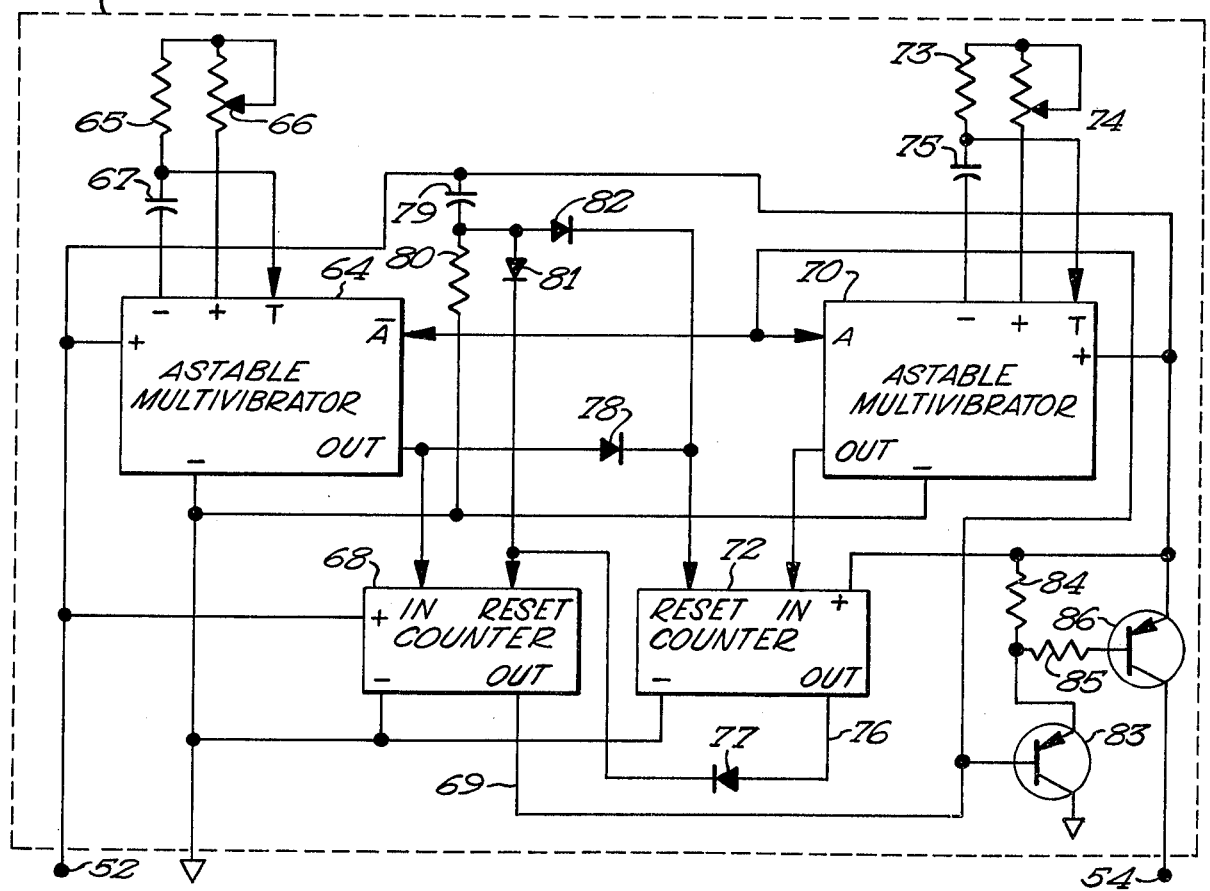

Turning now to FIGS. 9 and 10, there is shown in detail a circuit diagram of the tranmitter and receiver of the electro-spinal instrumentation system. As mentioned hereinbefore, the transmitter 24 cyclically develops at its antenna 18 a train of radio frequency energy stimulating impulses at a predetermined rate, pulse-width and amplitude that are adjustable in the circuit, the pulse train duration also being adjustable by further elements of the circuit. In the circuit of FIGS. 9 and 10, the transmitter includes a power source consisting, for example, of a 9-volt battery 50 of a conventional dry cell type that may be depleted through use of the transmitter and replaced as necessary by the patien*. An on-off switch 51 is connected in series with the battery and with the input terminal 52 of a cycler circuit 53, the details of which will be explained with respect to FIG. 10. The cycler circuit 53 comprises a cyclic timer with on and off times individually selectable at the time of manufacture from 1 millisecond to 1 hour. In this particular application, the cycler may be designed to have an on-time adjustable from 1 to 5 seconds and an off-time adjustable from 5 to 25 seconds. During the on-time of the cycler circuit 53, supply voltage is applied from the output terminal 54 to the pulse rate oscillator circuit 55. At all times that switch 51 is closed, supply voltage is applied by conductor 56 to the pulse width control circuit 58 and the radio frequency oscillator circuit 60, but neither of these circuits can operate as long as source voltage is not applied to the pulse rate oscillator circuit 55. A filter capacitor 61 is connected across the input terminal 52 and circuit ground.

The rate oscillator circuit 55 produces a train of pulses recurring at a predetermined rate so long as supply voltage appears at the output terminal 54 of the cycler circuit 53, and the train of pulses is applied to the pulse width control circuit 58. The pulse width control circuit 58 may comprise a mono-stable multi-vibrator triggered by each pulse developed by the circuit 55 to produce a further pulse, the multi-vibrator having an adjustable resistor element for adjusting the width of its output pulse. The radio frequency oscillator 60 ocillates whenever an output pulse is received from the pulse width control circuit 58 at a preselected frequency such as 460 kilohertz, resulting in a train of pulses each having a predetermined pulse width and recurring at a preset rate during the on-time of cycler 53, each pulse thereby comprising a burst of radio frequency energy as depicted as wave form A in FIG. 1. In the radio frequency oscillator circuit 60, an amplitude control circuit is provided to adjust the voltage amplitude of the radio frequency energy pulses.

The antenna 18 is electrically connected to the output of the radio frequency oscillator circuit 60, and, as described hereinbefore, is used to couple the radio frequency pulses through the skin of the patient to the receiver circuit. As depicted in FIG. 1, the energy from the transmitting antenna is coupled with an antenna 62 within the receiver 17 where it is then detected and applied to the muscle through the leads 16 and electrodes 15.

Turning now to the circuit of FIG. 10, the battery power source 50 is electrically connected in series through the switch 51 to the input terminal 52. The cycler circuit 53 comprises a first astable multi-vibrator 64 that oscillates at a frequency determined by the external R-C time components 65, 66 and 67. A first binary counter 68 receives impulses from the first astable multi-vibrator 64 until it reaches a predetermined count, whereupon the counter 68 develops or produces a high output state on conductor 69 that is conducted to the $\overline{A}$ input of oscillator 64 to halt its operation and is also conducted to the $\overline{A}$ input of a second astable multi-vibrator 70. Astable multi-vibrator 70 responds to the high state at its A input to generate and apply pulses to second binary counter 72 which counts the number of pulses developed by the second astable multi-vibrator 70 until it reaches a preselected count. The frequency of the pulses developed by the second astable multi-vibrator 70 is governed by R-C time components 73, 74 and 75.

When the full count is reached by the second counter 72, it develops a high output state on conductor 76 which is conducted through diode 77 to the Reset input of the first counter 68 which in response thereto terminates the high output state on conductor 69. At that moment, the low output state applied to the $\overline{A}$ input of the first astable multi-vibrator 64 causes it to start to oscillate, and the low output state applied to the $\overline{A}$ input of the second astable multi-vibrator 70 causes it to cease oscillating. The output signal developed by the first astable multi-vibrator 64 is conducted by conductor 78 to the Reset input of counter 72 to terminate the high output state on conductor 76, so that counter 68 is no longer reset and can count.

The oscillation frequencies of the astable multi-vibrators 64 and 70 are established by the charge times of the capacitors 67 and 75, respectively, that are variable by adjustment of variable resistors 66 and 74, respectively.

In order to achieve consistent operation of the cycler 53, a Reset circuit comprising capacitor 79, resistor 80 and diodes 81 and 82 coupled between the power supply input 52 and the Reset inputs of counters 68 and 70 provides that, when the power supply is applied by the closing switch 51 (FIG. 9) by the patient, the counts in both counters are Reset to zero by supply voltage conducted through capacitor 79 and diodes 81 and 82. As supply voltage rapidly increased across capacitor 79, the Reset signal rapidly dissipates and the counters are rendered operational in the manner described, and the cycler circuit 53 operates at the start of its on-time cycle.

As mentioned hereinbefore, supply voltage is applied to rate oscillator circuit 55 during the on-time cycle of the cycler 53, that is, the time following achievement of the full count in first counter 68 and while second counter 72 is counting. More specifically, the high or relatively positive output state of the first counter 68 is applied by conductor 69 to the base of a switching transistor 83, the emitter-collector path of which is coupled between ground potential and the junction of resistors 84 and 85. Resistor 84 is coupled to battery supply voltage, and resistor 85 is connected to the base of a power switching transistor 86. The positive going voltage applied to the base of transistor 83 turns transistor 83 on which lowers the voltage at the base of transistor 86 thus causing transistor 86 to turn on and allows battery current to flow between input 52 and output 54. Thus battery voltage is applied through transistor 86 to the rate oscillator circuit 55.

The astable multi-vibrators and counters are C-Mos integrated circuits of types RCA-4047 and RCA-4040, respectively, available from RCA Corporation.

Referring now particularly to the rate oscillator circuit 55 of FIG. 9, it comprises a reference voltage source including the transistor 88, the resistors 90, 91, 92 and 93, the capacitor 94 and the diode 95 which apply a reference voltage to an oscillator portion of the circuit 55 comprising a programmable uni-junction transistor (PUT) 96, a variable rate control resistor 97, resistor 98 and capacitor 99. The source voltage is applied across reference voltage divider resistors 90 and 91, the junction of which are connected to the base of transistor 88. Transistor 88 is thereby normally biased to conduct source voltage to the junction of resistor 92 and capacitor 94, less the forward voltage drop of transistor 88. The source voltage thus applied through resistors 92, 93 and diode 95 is conducted to the gate of the PUT 96 to establish a reference voltage level at its gate. Resistors 92 and 93 are selected to have relatively low and high impedances, respectively, and therefore, capacitor 94, resistor 92 and diode 95 present a low impedance voltage source in the forward direction of conduction, to the gate of PUT 96. Conversely, to prevent the PUT 96 from being latched on by reverse current flow, the resistor 93 presents a high impedance to the gate. The rate of production of the pulses is controlled by the RC timing circuit comprising the variable pulse rate control resistor 97, the resistor 98 and the capacitor 99 and the PUT 96. As source voltage is applied across the RC timing circuit, voltage on capacitor 99 increases until that voltage reflected at the anode of PUT 96 exceeds the reference voltage at its gate, whereupon the PUT 96 is rendered conductive to produce an output pulse at its cathode. When the PUT 96 is rendered conductive, the voltage on capacitor 99 is discharged through the resistors 100 and 102 only to the reference potential on its gate. The PUT 96 is rendered conductive so long as the positive voltage applied to its anode exceeds that applied to its gate. The values of capacitor 99 and resistors 100 and 102 are selected to provide a positive spike output signal that is applied to the pulse width control circuit 58 on conductor 103. The rate of oscillation of the circuit 55, and thus the rate at which stimulation pulses are produced is selectable by varying the pulse gate control resistor 99.

The pulse width control circuit 58 operates as a monostable multi-vibrator in response to the positive spike output signal of the circuit 55 to produce an output pulse having a uniform pulse width that is applied to the input of the RF oscillator circuit 60.

Since the cathode of PUT 96 is normally at ground potential reflected through the circuit of resistors 100 and 102, the transistor 104 is concurrently normally non-conductive. The pulse width control elements of circuit 58 comprises variable pulse width control resistor 106, resistor 108, capacitor 110 and resistor 112 The junction of resistor 112 and capacitor 110 is connected to the collector of normally non-conductive transistor 104, and capacitor 110 normally charges to a predetermined voltage of positive polarity at the aforementioned junction. A second transistor 114 is connected at its base to the junction of resistor 108 and capacitor 110, and its collector-emitter path is connected in series with resistor 116 across supply voltage.

The junction of the resistor 116 and the collector of transistor 114 is coupled by conductor 118 to the junction of resistors 100 and 102. Normally, while transistor 104, is non-conductive, transistor 114 is conductive, reflecting ground potential back to conductor 118.

When a spike potential is produced at the cathode of PUT 96 and applied by conductor 103 to the base of transistor 104, transistor 104 is rendered conductive. Capacitor 110 discharges through transistor 104 and resistors 106 and 108, and simultaneously renders transistor 114 non-conductive, thus raising the potential on conductor 118. The increased potential on conductor 118 is reflected through resistor 110 and conductor 103 back to the base of transistor 104, latching it in positive feedback conduction for so long as capacitor 110 continues to discharge, that time period constituting the pulse width of the transmitted stimulating impulses. The output pulse of the pulse width control circuit 58 is a square wave appearing on the conductor 119.

The conductor 119 is coupled to the input of the RF oscillator circuit 60, and the output pulse produced thereon triggers the oscillator circuit 60 into producing an RF transmission signal of a pulse width determinable by the circuit 58 at a recurring rate established by the circuit 55 during the on-time period of the cycler 53. The amplitude of the transmitted RF stimulation signal is adjustable by an amplitude control element of the circuit 60.

The RF oscillator circuit 60 includes: (1) a Colpitts oscillator comprising the transistors 120 and 122, the variable inductor 114, the capacitors 126 and 128, and the resistor 130 that produces an oscillatory signal at a predetermined frequency, e.g., 460 KHz, during the duration of the output of circuit 55; (B) an emitter-follower amplifier responsive to the RF signal comprising transistor 130 and resistors 132, 134, and 136 and capacitor 138 for capacitively coupling the RF signal to; (3) a class C operating amplifier comprising transistor 140, inductor 142, variable amplitude control resistor 144 and resistor 146 for further amplifying and isolating the RF signal from the D.C. source voltage; and (4) an oscillatory antenna circuit comprising capacitors 148 and 150 that, in conjunction with the inductance of antenna 18 oscillates sympathetically at the same radio frequency, e.g., 460 KHz.

In greater detail of operation, the Colpitts oscillator circuit includes inductive and capacitive values that, when coupled to source potential through conduction of transistors 120 and 122 in response to the positive output pulse on conductor 119, establishes a rate of radio frequency oscillation at the base of transistor 130. Transistors 130 and 140 amplify and reflect the oscillations to the resonating antenna circuit, and the inductor 142 provides a low impedance to high frequency signals and a high impedance to the D.C. source potential, so that transistor 140 can operate in the Class C state. The current amplification factor of transistor 140 is adjustable by varying resistor 144, a procedure that normally is done by the surgeon at the time of implant and during post-operative treatment.

The radio frequency signals are detected by a sympathetically tuned receiver circuit 17, comprising the inductance 62 of the receiver antenna, capacitors 154, 156 and 158, diode 160 and resistor 162, which are all connected in a well known receiver configuration to detect 460 KHz signals, rectify the detected signals and filter them to produce the pulse train of wave from B of FIG. 1. The leads 16 that couple the received RF stimulation signals to the remote stimulation sites are connected as shown to the receiver circuit 17.

It is contemplated that the system of the present invention may be advantageously employed with three electrodes, two negative stimulating electrodes and one positive indifferent electrode. It is further contemplated that the stimulation employed will be intermittent bursts of bi-phasic square wave pulses, the stimulation being provided for one to five with intervals between stimulation of five to twenty-five seconds. As is known in the art, such intermittent stimulation prevents muscle fatigue. A duty cycle (ratio of on time to off time) of one to five has been found to be advantageous for its further reduction of muscle fatigue. It is further contemplated that the pulses will fall within the range of 30 to 60 pulses per second with an amplitude of approximately 3 volts. During the determination of the optimal location and penetration depth for the electrode, however, it may be desirable to employ a stimulation amplitude of 10 volts or more. It is expected that, during treatment, stimulation will be provided for a period of 8 to 10 hours during sleep and that treatment will continue at least until the patient has achieved maturity, most likely until the patient is 16 to 18 years of age. However, as the desirable correction is approached treatment may be conducted on an intermittent (non-daily) basis to reduce the possibility of over correction.

Obviously, many modifications and variations of the present invention are possible in light of the above teachings. For example, other electrode configurations may be employed in place of the helical electrode described in the preferred embodiment. Such electrodes may take the form of a needle, with or without a barb, and extend from the electrode body 42 in the same direction as the helical electrode to be positioned within the paraspinal muscles through the use of the sleeve 26 and tool 35. It is therefore to be understood that, within the scope of the appended claims, the invention may be practiced otherwise than as specifically described.

What is claimed is:

1. Apparatus for positioning and securing and electrode within paraspinal muscles for use in the electrical treatment of spinal curvature, said apparatus comprising;
   sleeve means;
   probe means inserted within said sleeve means, said probe means including blunt tip means extending from said sleeve means when said probe means is inserted therein for penetrating said muscle and means engaging said sleeve means for carrying said sleeve means with said probe means during said muscle penetration while allowing said probe means to be withdrawn from said sleeve means and said muscle after said penetration; and
   elongated means inserted within said sleeve means after withdrawal of said probe means, said elongated means including means engageable with said electrode for imparting a force thereto while allowing a disengagement with said electrode in one direction along the longitudinal axis of said elongated means.

2. The apparatus of claim 1 wherein said probe means tip means is provided with means for optimizing the position of said sleeve means within said paraspinal muscle.

3. The apparatus of claim 2 wherein said optimizing means comprises electrode means for delivering electrical energy to said paraspinal muscle.

4. Apparatus for positioning and securing within muscle tissue a rotationally inserted electrode having tab means and a conductive lead extending longitudinally therefrom, said apparatus comprising:
   sleeve means one end of which penetrates said tissue to a desired depth within said muscle; and
   elongated means insertable through the other end of said sleeve means for delivering and securing said electrode within said muscle tissue at a position beyond said one sleeve means end, said elongated means including slot means on one end thereof for accepting said tab means and imparting a rotational force thereto while allowing a disengagement between said tab means and slot means in one direction along the longitudinal axis of said elongated means and said slot means including recess means extending from said one elongated means end in said one direction for accepting said conductive lead within said elongated means from said one elongated means end.

5. The apparatus of claim 4 wherein said sleeve means is provided with a slot throughout its length, said slot being at least as large as said conductive lead.

6. A method of electrode placement for use in an electrical treatment of spinal curvature comprising the use of:
   a. inserting needle electrodes within the paraspinal muscles adjacent said spinal curvature;
   b. stimulating the paraspinal muscles with an electrical signal applied to said needle electrodes;
   c. determining the relative effect of the stimulated muscle reaction on said spinal curvature;
   d. repositioning said needle electrodes within the paraspinal muscles;
   e. repeating steps (b), (c) and (d) to establish the electrode insertion sites which maximize corrective, stimulated muscle contraction;
   f. removing said needle electrodes;
   g. inserting a blunt probe fitted with a sleeve within said paraspinal muscle at each of the sites established in step (e), said probes having an electrode extending from said sleeve;
   h. stimulating said paraspinal muscles with an electrical signal applied to said probe electrodes;
   i. determining the relative effect of the stimulated muscle reaction on said spinal curvature;
   j. altering the amount of penetration of said probes in said paraspinal muscles;
   k. repeating steps (h), (i) and (j) to establish the electrode depth which maximizes corrective, stimulated muscle contraction;
   l. removing said probes from said paraspinal muscle while leaving said sleeves within said muscle at the sites and depths established in steps (e) and (k), respectively;
   m. inserting electrodes having conductive leads through said sleeves and into engagement with said muscle at the sites and depths established in steps (e) and (k), respectively;
   n. removing said sleeves while leaving said electrodes in engagement with said muscle;

7. The method of claim 6 wherein step (m) comprises the steps of:

o. positioning a helical electrode on one end of an elongated tool, said elongated tool securing said electrode against rotational movement relative thereto while showing said electrode to be withdrawn from said tool in one direction along the longitudinal axis of said tool;

p. inserting said one end of said elongated tool through one of said sleeves;

q. advancing said electrode into contact with said muscle;

r. rotating said elongated tool to engage said helical electrode with said muscle;

s. removing said elongated tool while leaving said electrode in engagement with said muscle; and t. repeating steps (o) through (s) for each sleeve.

8. Apparatus including an electrode for positioning and securing said electrode within paraspinal muscles for use in the electrical treatment of spinal curvature, said apparatus comprising:

sleeve means;

probe means inserted within said sleeve means, said probe means including blunt tip means extending from said sleeve means when said probe means is inserted therein for penetrating said muscle and means engaging said sleeve means for carrying said sleeve means with said probe means during said muscle penetration while allowing said probe means to be withdrawn from said sleeve means and said muscle after said penetration; and elongated means inserted within said sleeve means after withdrawal of said probe means, said elongated means including means engageable with said electrode for imparting a force thereto while allowing a disengagement with said electrode in one direction along the longitudinal axis of said elongated means.

9. The apparatus of claim 8 wherein said electrode is a helical electrode having a tab, said means engageable with said electrode comprising slot means in said elongated means for accepting said electrode tab and imparting a rotational force thereto.

10. The apparatus of claim 9 wherein said electrode is secured to, and in electrical communication with, a conductive lead, said elongated means including recess means for accepting said conductive lead.

11. The apparatus of claim 10 wherein said sleeve means is provided with a slot throughout its length, said slot being at least as large as said conductive lead.

12. The apparatus of claim 11 wherein said probe means tip means is provided with means for optimizing the depth of penetration of said sleeve means in said paraspinal muscle.

13. The apparatus of claim 12 wherein said optimizing means comprises electrode means for delivering electrical energy to said paraspinal muscle.

14. Apparatus for establishing the optimum position of an electrode for use in the treatment of disease syndromes by the selective application of electrical stimulation to the body and maintaining said optimum position until positioning and securement of said electrode comprising sleeve means and probe means removable inserted within said sleeve means through one end thereof, said probe means including tip means extending from the other end of said sleeve means for penetrating body tissue and electrode means carried by said tip means in predetermined relation to said sleeve means other end, said probe means being removable from said sleeve means and said body tissue through said one end of said sleeve means and said electrode means being adapted for connection to a source of electrical stimulation energy.

15. The apparatus of claim 14 wherein said tip means comprises blunt, muscle-penetration means.

16. A method of establishing the optimum placement of electrodes to be used in an electrical treatment of spinal curvature comprising the steps of:

a. inserting needle electrodes within the paraspinal muscles adjacent said spinal curvature;

b. stimulating the paraspinal muscles with an electrical signal applied to said needle electrodes;

c. determining the relative effect of the stimulated muscle reaction on said spinal curvature;

d. repositioning said needle electrodes within the paraspinal muscles;

e. repeating steps (b), (c) and (d) to establish the electrode insertion sites which maximize corrective, stimulated muscle contraction;

f. removing said needle electrodes;

g. inserting blunt probe electrodes within said paraspinal muscle at each of the sites established in step (c);

h. stimulating said paraspinal muscles with an electrical signal applied to said probe electrodes;

i. determining the relative effect of the stimulated muscle reaction on said spinal curvature;

j. altering the amount of pentration of said probes in said paraspinal muscles;

k. repeating steps (h), (i) and (j) to establish the electrode depth which maximizes corrective, stimulated muscle contraction.

17. A method of establishing the optimum electrode penetration depth within muscle tissue at a predetermined site for use in the treatment of disease syndromes through the selective application of electrical stimulation to the body comprising the steps of:

a. inserting muscle penetrating a probe within said muscle tissue at said predetermined site, said probe having a probe electrode;

b. applying a body stimulation signal to said probe electrode;

c. determining the relative effect of the body reaction to said stimulation signal;

d. altering the amount of muscle tissue penetration of said probe at said predetermined site; and e. repeating steps (b), (c) and (d) to establish the electrode depth which maximizes the desired body reaction.

18. The method of claim 17 wherein the step of inserting comprises the step of inserting a probe fitted with a sleeve, said probe electrode having a predetermined relation to said sleeve, the method further comprising the steps of:

f. removing said probe while leaving said sleeve at said predetermined site and at the depth established in step (e).

19. The method of claim 18 further comprising the steps of:

g. inserting an electrode through said sleeve and into engagement with the body tissue at said predetermined site and at the depth established in step (e); and h. removing said sleeve while leaving said electrode in engagement with said body tissue.

* * * * *

UNITED STATES PATENT AND TRADEMARK OFFICE
CERTIFICATE OF CORRECTION

PATENT NO. : 4,026,301
DATED : May 31, 1977
INVENTOR(S) : HARRY G. FRIEDMAN and ROBERT W. WICKHAM, JR.

It is certified that error appears in the above-identified patent and that said Letters Patent are hereby corrected as shown below:

Col. 4, line 45, "not" should be --now--.

Col. 7, line 9, "tranmitter" should be --transmitter--.

Col. 7, line 50, "ocillates" should be --oscillates--.

Col. 10, line 36, "output of circuit 55;" should be --output pulse of circuit 55;--.

Col. 10, line 36, "(B)" should be --(a)--.

Claim 1, Col. 11, line 46, "securing and" should be --securing an--.

Claim 4, Col. 12, line 10, "penetrates said tissue" should be --penetrates said muscle tissue--.

Claim 6, Col. 12, line 31, "use of" should be --steps of--.

Claim 14, Col. 13, line 61, "removable" should be --removably--.

Signed and Sealed this

Tenth Day of January 1978

[SEAL]

Attest:

RUTH C. MASON
Attesting Officer

LUTRELLE F. PARKER
Acting Commissioner of Patents and Trademai